(12) United States Patent
Ritter et al.

(10) Patent No.: US 8,143,450 B1
(45) Date of Patent: *Mar. 27, 2012

(54) PROCESS FOR THE PREPARATION OF DERIVATIVES OF TETRAAMINOBENZENE

(75) Inventors: Joachim C. Ritter, Wilmington, DE (US); Ekaterini Korovessi, Wilmington, DE (US); Rajiv Dhawan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 389 days.

This patent is subject to a terminal disclaimer.

(21) Appl. No.: 12/337,701

(22) Filed: Dec. 18, 2008

Related U.S. Application Data

(60) Provisional application No. 61/014,526, filed on Dec. 18, 2007, provisional application No. 61/014,551, filed on Dec. 18, 2007.

(51) Int. Cl.
*C07C 211/00* (2006.01)

(52) U.S. Cl. ......... 564/306; 562/405; 562/480; 564/305

(58) Field of Classification Search .................. None
See application file for complete search history.

(56) References Cited

U.S. PATENT DOCUMENTS

| | | | | |
|---|---|---|---|---|
| 3,174,947 | A * | 3/1965 | Marvel et al. | 528/331 |
| 4,533,692 | A * | 8/1985 | Wolfe et al. | 524/417 |
| 5,041,522 | A * | 8/1991 | Dang et al. | 528/183 |
| 5,674,969 | A | 10/1997 | Sikkema et al. | |
| 6,040,478 | A | 3/2000 | Sikkema et al. | |
| 2006/0287475 | A1 | 12/2006 | Allen et al. | |

FOREIGN PATENT DOCUMENTS

JP 2003-292476 * 10/2003

OTHER PUBLICATIONS

Blanksma, Chemisch Weekblad, 1913, 9, 968-73.*
Cotton and Wilkinson, Advanced Inorganic Chemistry, 2nd Edition, 1966, Published by Interscience New York.

* cited by examiner

*Primary Examiner* — Sudhakar Katakam

(57) ABSTRACT

A process is provided for preparing complexes of 1,2,4,5-tetraminobenzene with an aromatic diacid. The process design eliminates costly intermediate drying and recrystallization steps. Handling of solid materials with possible skin sensitizing properties and toxicity is avoided, thereby eliminating human and environmental exposure.

19 Claims, 2 Drawing Sheets

PROCESS FOR THE PREPARATION OF DERIVATIVES OF TETRAAMINOBENZENE

This application claims priority under 35 U.S.C. §119(e) from, and claims the benefit of, U.S. Provisional Application No. 61/014,526, filed Dec. 18, 2007, and U.S. Provisional Application No. 61/014,551, filed Dec. 18, 2007, each of which is by this reference incorporated in its entirety as a part hereof for all purposes.

TECHNICAL FIELD

The disclosure relates to methods of making complexes of 1,2,4,5-tetraminobenzene with aromatic diacids.

BACKGROUND

The synthesis of preferred polybenzimidazole-based, high-performance fibers typically involves the selective condensation polymerization of 1,2,4,5-tetraminobenzene ("TAB") with various substituted and unsubstituted aromatic diacids or derivatives thereof.

Previously known polymers TAB-based polymers were synthesized, for example, from TAB.4HCl and acid chlorides, but they had a molecular weight or intrinsic viscosity that was too low to produce fibers with desirably high mechanical properties such as high tensile strength fiber.

When TAB is polymerized with a monomer such as 2,5-dihydroxyterephthalic acid ("DHTA"), it is desired that the ratio of tetraamine to diacid be as close to 1:1 as possible to achieve a high molecular weight polymer of fiber-grade purity. Production of high molecular weight polymer typically requires a high space time yield process wherein a 1:1 complex between diacid and tetraamine is polymerized. In such a process, there are also safety concerns, especially with respect to sensitizing properties of some intermediates, that need to be addressed There thus remains a need for a process for the production of a suitable TAB-diacid monomer complex that can be polymerized to a high molecular weight polymer material for producing high-performance fibers, wherein the complex is formed from a stable precursor without isolation of intermediates.

SUMMARY

The inventions disclosed herein include processes for the preparation of a tetraminobenzene complex, processes for the preparation of products into which a tetraminobenzene complex can be converted, the use of such processes, and the products obtained and obtainable by such processes.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

One embodiment of this invention provides a process for preparing a complex that comprises 1,2,4,5-tetraminobenzene and the aromatic diacid XYTA [which is represented by the structure of the following Formula (I)]:

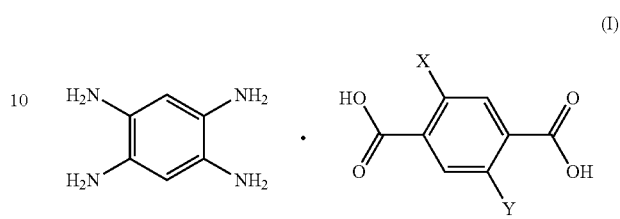

(I)

wherein X and Y are each independently selected from the group consisting of H, OH, SH, methyl, ethyl, F, Cl and Br; comprising (a) nitrating 1,3-dihalobenzene, which is represented by the structure of the following Formula (II):

II wherein each Z is independently Cl or Br, to produce 1,3-dihalo-4,6-dinitrobenzene;

(b) heating a suspension of the 1,3-dihalo-4,6-dinitrobenzene, and contacting it with $NH_3$ to aminate the 1,3-dihalo-4,6-dinitrobenzene and convert it to 1,3-diamino-4,6-dinitrobenzene;

(c) forming a slurry of the 1,3-diamino-4,6-dinitrobenzene with water, and contacting the slurry with hydrogen and a hydrogenation catalyst to hydrogenate the 1,3-diamino-4,6-dinitrobenzene and produce 1,2,4,5-tetraminobenzene;

(d) contacting the 1,2,4,5-tetraminobenzene produced in (c) with an aqueous solution comprising 1 to 6 equivalents of acid per mol of 1,2,4,5-tetraminobenzene, and, optionally, heating the solution to dissolve the 1,2,4,5-tetraminobenzene; and (e) combining the dissolved 1,2,4,5-tetraminobenzene with
  (i) 0 to 5 equivalents of an acid;
  (ii) 0 to 5 equivalents of a base;
  (iii) optionally, a buffer solution; and
  (iv) an XYTA source selected from XYTA and $M_2$XYTA as represented by the structure of the following Formula (III):

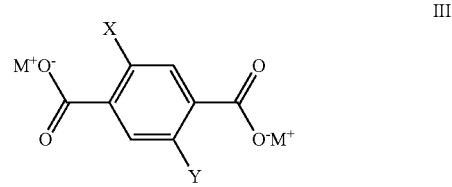

III wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex.

A further embodiment of this invention provides a process for preparing a complex that comprises 1,2,4,5-tetraminobenzene and the aromatic diacid XYTA [which is represented by the structure of the following Formula (I)]:

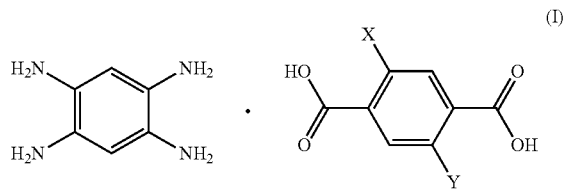

wherein X and Y are each independently selected from the group consisting of H, OH, SH, methyl, ethyl, F, Cl and Br; comprising
(a) nitrating 1,3-dihalobenzene, which is represented by the structure of the following Formula (II):

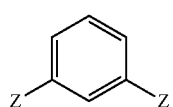

wherein each Z is independently Cl or Br, in a reaction mixture comprising nitric acid, oleum or $SO_3$, and $H_2SO_4$, wherein
(i) the concentration of nitric acid is about 2.0 to about 2.3 moles per mole of 1,3-dihalobenzene;
(ii) the concentration of $SO_3$ is about 1 to about 3 moles per mole of 1,3-dihalobenzene; and
(iii) the concentration of 1,3-dihalobenzene in the reaction mixture is between about 12 and about 24 weight percent; and
(iv) the temperature of the reaction mixture does not exceed 120° C.; to produce 1,3-dihalo-4,6-dinitrobenzene;
(b) filtering the reaction mixture to separate the 1,3-dihalo-4,6-dinitrobenzene therefrom, while recycling the sulfuric acid mother liquor;
(c) washing the 1,3-dihalo-4,6-dinitrobenzene with water, or acid then water, then with $NH_4OH$, and then mixing it with a solvent as a suspension;
(d) heating the suspension formed in step (c) to a temperature in the range of about 100° C. to about 160° C. and contacting it with $NH_3(g)$ to aminate the 1,3-dihalo-4,6-dinitrobenzene and convert it to 1,3-diamino-4,6-dinitrobenzene;
(e) filtering the reaction mixture to separate the 1,3-diamino-4,6-dinitrobenzene therefrom; and washing the 1,3-diamino-4,6-dinitrobenzene with a solvent and then water,
(f) forming a slurry of the 1,3-diamino-4,6-dinitrobenzene with water, and transferring the slurry to a hydrogenation reactor containing a hydrogenation catalyst to form a reaction mixture;
(g) contacting the reaction mixture formed in step (f) with hydrogen at a pressure in the range of about 0.31 to about 3.45 MPa and a temperature in the range of about 20° C. to about 100° C. to hydrogenate the 1,3-diamino-4,6-dinitrobenzene and produce 1,2,4,5-tetraminobenzene;
(h) contacting the 1,2,4,5-tetraminobenzene produced in (g) with an aqueous solution comprising 1 to 6 equivalents of acid per mol of 1,2,4,5-tetraminobenzene, and, optionally, heating the solution to dissolve the 1,2,4,5-tetraminobenzene;
(i) filtering the reaction mixture to remove the spent hydrogenation catalyst;
(j) combining the filtered reaction mixture with
(i) 0 to 5 equivalents of an acid selected from the group consisting of HCl, acetic acid, $H_2SO_4$ and $H_3PO_4$;
(ii) 0 to 5 equivalents of an organic base or an inorganic base;
(iii) optionally, a buffer solution; and
(iv) an XYTA source selected from XYTA and $M_2$XYTA as represented by the structure of the following Formula (III):

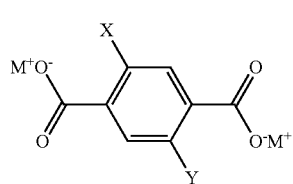

wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex; and
(k) cooling, filtering and washing the precipitated complex.

Another embodiment of this invention provides a process for preparing a complex that comprises 1,2,4,5-tetraminobenzene and the aromatic diacid XYTA [which is represented by the structure of the following Formula (I)]:

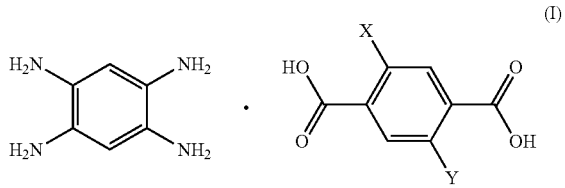

wherein X and Y are each independently selected from the group consisting of H, OH, SH, methyl, ethyl, F, Cl and Br; comprising
(a) nitrating 1,3-dihalobenzene, which is represented by the structure of the following Formula (II):

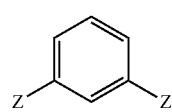

wherein each Z is independently Cl or Br, to produce 1,3-dihalo-4,6-dinitrobenzene;
(b) heating a suspension of the 1,3-dihalo-4,6-dinitrobenzene, and contacting it with $NH_3$ to aminate the 1,3-dihalo-4,6-dinitrobenzene and convert it to 1,3-diamino-4,6-dinitrobenzene;
(c) forming a slurry of the 1,3-diamino-4,6-dinitrobenzene with water, and contacting the slurry with hydrogen and a hydrogenation catalyst to hydrogenate the 1,3-diamino-4,6-dinitrobenzene and produce 1,2,4,5-tetraminobenzene;

(d) contacting the 1,2,4,5-tetraminobenzene produced in (c) with an aqueous solution comprising 1 to 6 equivalents of acid per mol of 1,2,4,5-tetraminobenzene, and, optionally, heating the solution to dissolve the 1,2,4,5-tetraminobenzene;

(e) adding an acid to the dissolved 1,2,4,5-tetraminobenzene to form and precipitate a salt of the 1,2,4,5-tetraminobenzene;

(f) combining the precipitated salt of the 1,2,4,5-tetraminobenzene with
(i) 0 to 5 equivalents of an acid;
(ii) 0 to 5 equivalents of a base;
(iii) optionally, a buffer solution; and
(iv) an XYTA source selected from XYTA and $M_2$XYTA as represented by the structure of the following Formula (III):

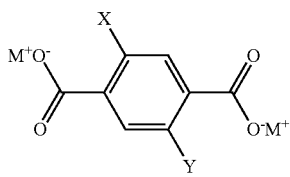

wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex.

Yet another embodiment of this invention provides a process for preparing a complex that comprises 1,2,4,5-tetraminobenzene and the aromatic diacid XYTA [which is represented by the structure of the following Formula (I)]:

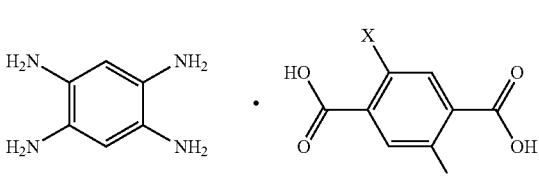

wherein X and Y are each independently selected from the group consisting of H, OH, SH, methyl, ethyl, F, Cl and Br; comprising (a) nitrating 1,3-dihalobenzene, which is represented by the structure of the following Formula (II):

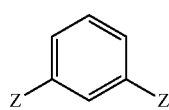

wherein each Z is independently Cl or Br, in a reaction mixture comprising nitric acid, oleum or $SO_3$, and $H_2SO_4$, wherein
(i) the concentration of nitric acid is about 2.0 to about 2.3 moles per mole of 1,3-dihalobenzene;
(ii) the concentration of $SO_3$ is about 1 to about 3 moles per mole of 1,3-dihalobenzene; and
(iii) the concentration of 1,3-dihalobenzene in the reaction mixture is between about 12 and about 24 weight percent; and
(iv) the temperature of the reaction mixture does not exceed 120° C.;
to produce 1,3-dihalo-4,6-dinitrobenzene;

(b) filtering the reaction mixture to separate the 1,3-dihalo-4,6-dinitrobenzene therefrom, while recycling the sulfuric acid mother liquor;

(c) washing the 1,3-dihalo-4,6-dinitrobenzene with water, or acid then water, then with $NH_4OH$, and then mixing it with a solvent as a suspension;

(d) heating the suspension formed in step (c) to a temperature in the range of about 100° C. to about 160° C. and contacting it with $NH_3(g)$ to aminate the 1,3-dihalo-4,6-dinitrobenzene and convert it to 1,3-diamino-4,6-dinitrobenzene;

(e) filtering the reaction mixture to separate the 1,3-diamino-4,6-dinitrobenzene therefrom; and washing the 1,3-diamino-4,6-dinitrobenzene with a solvent and then water;

(f) forming a slurry of the 1,3-diamino-4,6-dinitrobenzene with water, and transferring the slurry to a hydrogenation reactor containing a hydrogenation catalyst to form a reaction mixture;

(g) contacting the reaction mixture formed in step (f) with hydrogen at a pressure in the range of about 0.31 to about 3.45 MPa and a temperature in the range of about 20° C. to about 100° C. to hydrogenate the 1,3-diamino-4,6-dinitrobenzene and produce 1,2,4,5-tetraminobenzene;

(h) contacting the 1,2,4,5-tetraminobenzene produced in (g) with an aqueous solution comprising 1 to 6 equivalents of acid per mol of 1,2,4,5-tetraminobenzene, and, optionally, heating the solution to dissolve the 1,2,4,5-tetraminobenzene;

(i) filtering the reaction mixture to remove the spent hydrogenation catalyst;

(j) adding an acid to the filtered reaction mixture to form and precipitate a salt of the 1,2,4,5-tetraminobenzene, wherein the acid is selected from the group consisting of HCl, acetic acid, $H_2SO_4$, and $H_3PO_4$;

(k) cooling, filtering, washing and dissolving the precipitated 1,2,4,5-tetraminobenzene salt to form an aqueous solution thereof;

(l) combining the filtered reaction mixture with
(i) 0 to 5 equivalents of an acid selected from the group consisting of HCl, acetic acid, $H_2SO_4$ and $H_3PO_4$;
(ii) 0 to 5 equivalents of an organic base or an inorganic base;
(iii) optionally, a buffer solution; and
(iv) an XYTA source selected from XYTA and $M_2$XYTA as represented by the structure of the following Formula (III):

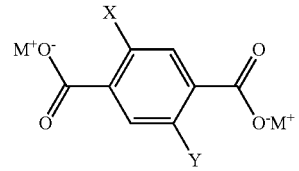

wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex; and (m) cooling, filtering and washing the precipitated complex.

Further provided is a process in which a TAB salt is produced in a separate step by adding acid to a previously-produced, filtered reaction mixture followed by cooling and filtration, dissolution of the TAB salt, formation and precipitation of the TAB.XYTA complex via addition of XYTA or XYTA salt, addition of aqueous base, and cooling. This embodiment produces higher purity TAB.XYTA complex without the need to use carbon bed filters and allows for more flexibility in terms of production (timing) and easier dosage.

BRIEF DESCRIPTION OF THE DRAWINGS

Various features and/or embodiments of this invention are illustrated in drawings as described below. These features and/or embodiments are representative only, and the selection of these features and/or embodiments for inclusion in the drawings should not be interpreted as an indication that subject matter not included in the drawings is not suitable for practicing the invention, or that subject matter not included in the drawings is excluded from the scope of the appended claims and equivalents thereof.

DETAILED DESCRIPTION

Figure 1:
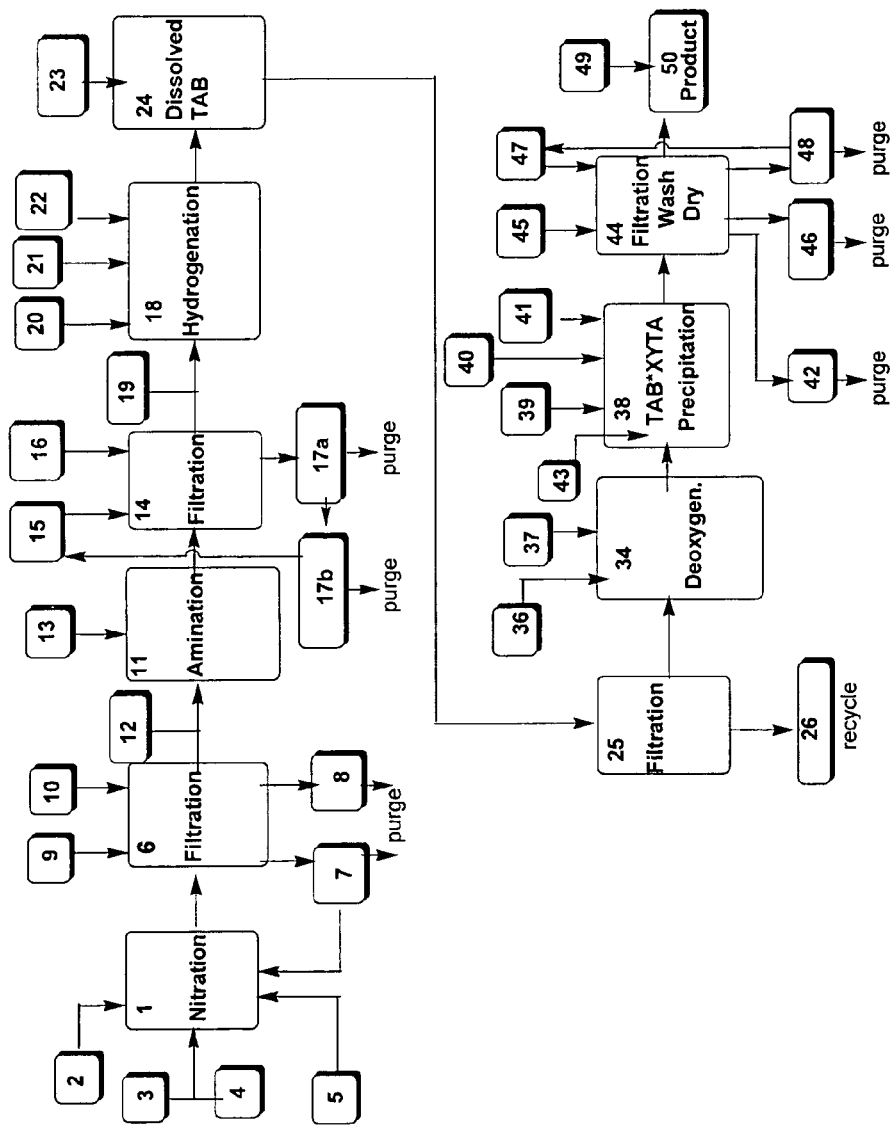
FIG. 1 is a schematic representation of one embodiment of the process described herein.

One embodiment of this invention provides a process for preparing a complex that comprises 1,2,4,5-tetraminobenzene and the aromatic diacid XYTA [which is represented by the structure of the following Formula (I)]:

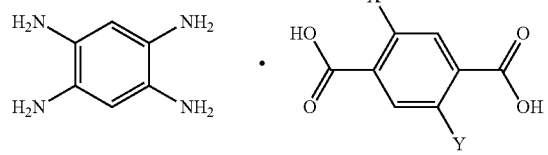

wherein X and Y are each independently selected from the group consisting of H, OH, SH, methyl, ethyl, F, Cl and Br; comprising (a) nitrating 1,3-dihalobenzene, which is represented by the structure of the following Formula (II):

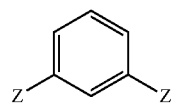

wherein each Z is independently Cl or Br, to produce 1,3-dihalo-4,6-dinitrobenzene;

(b) heating a suspension of the 1,3-dihalo-4,6-dinitrobenzene, and contacting it with $NH_3$ to aminate the 1,3-dihalo-4,6-dinitrobenzene and convert it to 1,3-diamino-4,6-dinitrobenzene;

(c) forming a slurry of the 1,3-diamino-4,6-dinitrobenzene with water, and contacting the slurry with hydrogen and a hydrogenation catalyst to hydrogenate the 1,3-diamino-4,6-dinitrobenzene and produce 1,2,4,5-tetraminobenzene;

(d) contacting the 1,2,4,5-tetraminobenzene produced in (c) with an aqueous solution comprising 1 to 6 equivalents of acid per mol of 1,2,4,5-tetraminobenzene, and, optionally, heating the solution to dissolve the 1,2,4,5-tetraminobenzene; and (e) combining the dissolved 1,2,4,5-tetraminobenzene with
(i) 0 to 5 equivalents of an acid;
(ii) 0 to 5 equivalents of a base;
(iii) optionally, a buffer solution; and
(iv) an XYTA source selected from XYTA and $M_2$XYTA as represented by the structure of the following Formula (III):

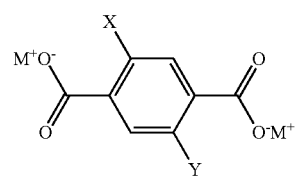

wherein M is K or Na, and wherein the molar ratio of XYTA to the 1,2,4,5-tetraminobenzene salt is from 1:1 to 1:1.1;

to adjust the pH of the mixture to between about 3 and about 10, and to produce and precipitate a Formula (I) complex.

As used herein, the term "XYTA" denotes 2-X-5-Y-terephthalic acid, where X and Y each independently selected from the group consisting of H, OH, SH, methyl, ethyl, F, Cl, and Br. One example is 2,5-dihydroxyterephthalic acid, in which X=Y=OH. The disodium or dipotassium salt of the diacid is represented by the term "$M_2$XYTA" where M is Na or K.

Step (b) may further involve one of the following alternative protocols for aminating the 1,3-dihalo-4,6-dinitrobenzene:

(i) (A) forming a suspension of 1,3-dihalo-4,6-dinitrobenzene in a mixture of solvent and water, wherein the suspension comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture); and (B) contacting the suspension with gaseous $NH_3$;

(ii) (A) forming a suspension of 1,3-dihalo-4,6-dinitrobenzene in solvent, (B) heating the suspension, and (C) contacting the heated suspension with an aqueous ammonia solution to form a reaction mixture that comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture); or (iii) contacting 1,3-dihalo-4,6-dinitrobenzene with a feed that comprises a solvent, $NH_3$ and water to form a reaction mixture that comprises a suspension of about 10 to about 25 wt % 1,3-dihalo-4,6-dinitrobenzene (based on the total weight of the whole reaction mixture) and about 2 to about 25 wt % water (based on the combined weight of water and solvent in the reaction mixture).

A further embodiment of this invention provides a process for preparing a complex that comprises 1,2,4,5-tetraminobenzene and the aromatic diacid XYTA [which is represented by the structure of the following Formula (I)]:

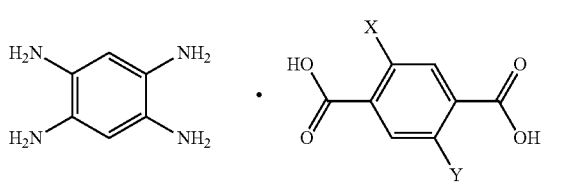
(I)

wherein X and Y are each independently selected from the group consisting of H, OH, SH, methyl, ethyl, F, Cl and Br; comprising (a) nitrating 1,3-dihalobenzene, which is represented by the structure of the following Formula (II):

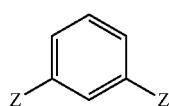
II wherein each Z is independently Cl or Br, in a reaction mixture comprising nitric acid, oleum or $SO_3$, and $H_2SO_4$, wherein
  (i) the concentration of nitric acid is about 2.0 to about 2.3 moles per mole of 1,3-dihalobenzene;
  (ii) the concentration of $SO_3$ is about 1 to about 3 moles per mole of 1,3-dihalobenzene; and
  (iii) the concentration of 1,3-dihalobenzene in the reaction mixture is between about 12 and about 24 weight percent; and
  (iv) the temperature of the reaction mixture does not exceed 120° C.;
to produce 1,3-dihalo-4,6-dinitrobenzene;

(b) filtering the reaction mixture to separate the 1,3-dihalo-4,6-dinitrobenzene therefrom, while recycling the sulfuric acid mother liquor;

(c) washing the 1,3-dihalo-4,6-dinitrobenzene with water, or acid then water, then with $NH_4OH$, and then mixing it with a solvent as a suspension;

(d) heating the suspension formed in step (c) to a temperature in the range of about 100° C. to about 160° C. and contacting it with $NH_3(g)$ to aminate the 1,3-dihalo-4,6-dinitrobenzene and convert it to 1,3-diamino-4,6-dinitrobenzene;

(e) filtering the reaction mixture to separate the 1,3-diamino-4,6-dinitrobenzene therefrom; and washing the 1,3-diamino-4,6-dinitrobenzene with a solvent and then water, (f) forming a slurry of the 1,3-diamino-4,6-dinitrobenzene with water, and transferring the slurry to a hydrogenation reactor containing a hydrogenation catalyst to form a reaction mixture;

(g) contacting the reaction mixture formed in step (f) with hydrogen at a pressure in the range of about 0.31 to about 3.45 MPa and a temperature in the range of about 20° C. to about 100° C. to hydrogenate the 1,3-diamino-4,6-dinitrobenzene and produce 1,2,4,5-tetraminobenzene;

(h) contacting the 1,2,4,5-tetraminobenzene produced in (g) with an aqueous solution comprising 1 to 6 equivalents of acid per mol of 1,2,4,5-tetraminobenzene, and, optionally, heating the solution to dissolve the 1,2,4,5-tetraminobenzene;

(i) filtering the reaction mixture to remove the spent hydrogenation catalyst;

(j) combining the filtered reaction mixture with
  (i) 0 to 5 equivalents of an acid selected from the group consisting of HCl, acetic acid, $H_2SO_4$ and $H_3PO_4$;
  (ii) 0 to 5 equivalents of an organic base or an inorganic base;
  (iii) optionally, a buffer solution; and
  (iv) an XYTA source selected from XYTA and $M_2$XYTA as represented by the structure of the following Formula (III):

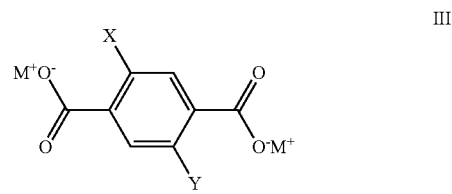
III wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex; and (k) cooling, filtering and washing the precipitated complex.

Another embodiment of this invention provides a process for preparing a complex that comprises 1,2,4,5-tetraminobenzene and the aromatic diacid XYTA [which is represented by the structure of the following Formula (I)]:

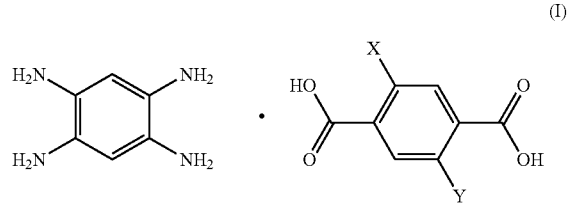
(I)

wherein X and Y are each independently selected from the group consisting of H, OH, SH, methyl, ethyl, F, Cl and Br; comprising (a) nitrating 1,3-dihalobenzene, which is represented by the structure of the following Formula (II):

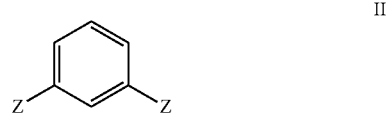
II wherein each Z is independently Cl or Br, to produce 1,3-dihalo-4,6-dinitrobenzene;

(b) heating a suspension of the 1,3-dihalo-4,6-dinitrobenzene, and contacting it with $NH_3$ to aminate the 1,3-dihalo-4,6-dinitrobenzene and convert it to 1,3-diamino-4,6-dinitrobenzene;

(c) forming a slurry of the 1,3-diamino-4,6-dinitrobenzene with water, and contacting the slurry with hydrogen and a hydrogenation catalyst to hydrogenate the 1,3-diamino-4,6-dinitrobenzene and produce 1,2,4,5-tetraminobenzene;

(d) contacting the 1,2,4,5-tetraminobenzene produced in (c) with an aqueous solution comprising 1 to 6 equivalents of acid per mol of 1,2,4,5-tetraminobenzene, and, optionally, heating the solution to dissolve the 1,2,4,5-tetraminobenzene;

(e) adding an acid to the dissolved 1,2,4,5-tetraminobenzene to form and precipitate a salt of the 1,2,4,5-tetraminobenzene;

(f) combining the precipitated salt of the 1,2,4,5-tetraminobenzene with
  (i) 0 to 5 equivalents of an acid;
  (ii) 0 to 5 equivalents of a base;
  (iii) optionally, a buffer solution; and
  (iv) an XYTA source selected from XYTA and $M_2$XYTA as represented by the structure of the following Formula (III):

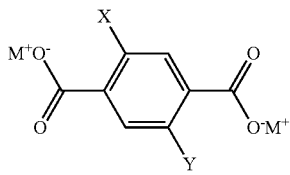

wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex.

A "TAB salt" or, equivalently, a "1,2,4,5-tetraminobenzene salt", is a compound formed by reaction of 1,2,4,5-tetraminobenzene with an acid such as HCl, acetic acid, $H_2SO_4$, or $H_3PO_4$. One example of a TAB salt is TAB.4HCl.

Yet another embodiment of this invention provides a process for preparing a complex that comprises 1,2,4,5-tetraminobenzene and the aromatic diacid XYTA [which is represented by the structure of the following Formula (I)]:

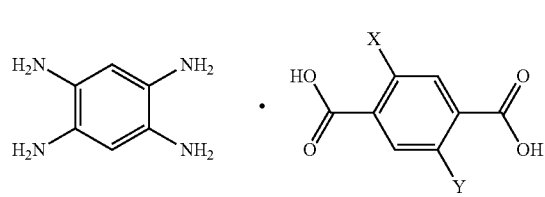

wherein X and Y are each independently selected from the group consisting of H, OH, SH, methyl, ethyl, F, Cl and Br; comprising (a) nitrating 1,3-dihalobenzene, which is represented by the structure of the following Formula (II):

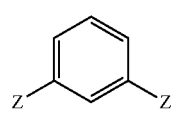

wherein each Z is independently Cl or Br, in a reaction mixture comprising nitric acid, oleum or $SO_3$, and $H_2SO_4$, wherein (i) the concentration of nitric acid is about 2.0 to about 2.3 moles per mole of 1,3-dihalobenzene;
(ii) the concentration of $SO_3$ is about 1 to about 3 moles per mole of 1,3-dihalobenzene; and
(iii) the concentration of 1,3-dihalobenzene in the reaction mixture is between about 12 and about 24 weight percent; and
(iv) the temperature of the reaction mixture does not exceed 120° C.; to produce 1,3-dihalo-4,6-dinitrobenzene;

(b) filtering the reaction mixture to separate the 1,3-dihalo-4,6-dinitrobenzene therefrom, while recycling the sulfuric acid mother liquor;

(c) washing the 1,3-dihalo-4,6-dinitrobenzene with water, or acid then water, then with $NH_4OH$, and then mixing it with a solvent as a suspension;

(d) heating the suspension formed in step (c) to a temperature in the range of about 100° C. to about 160° C. and contacting it with $NH_3(g)$ to aminate the 1,3-dihalo-4,6-dinitrobenzene and convert it to 1,3-diamino-4,6-dinitrobenzene;

(e) filtering the reaction mixture to separate the 1,3-diamino-4,6-dinitrobenzene therefrom; and washing the 1,3-diamino-4,6-dinitrobenzene with a solvent and then water, (f) forming a slurry of the 1,3-diamino-4,6-dinitrobenzene with water, and transferring the slurry to a hydrogenation reactor containing a hydrogenation catalyst to form a reaction mixture;

(g) contacting the reaction mixture formed in step (f) with hydrogen at a pressure in the range of about 0.31 to about 3.45 MPa and a temperature in the range of about 20° C. to about 100° C. to hydrogenate the 1,3-diamino-4,6-dinitrobenzene and produce 1,2,4,5-tetraminobenzene;

(h) contacting the 1,2,4,5-tetraminobenzene produced in (g) with an aqueous solution comprising 1 to 6 equivalents of acid per mol of 1,2,4,5-tetraminobenzene, and, optionally, heating the solution to dissolve the 1,2,4,5-tetraminobenzene;

(i) filtering the reaction mixture to remove the spent hydrogenation catalyst;

(j) adding an acid to the filtered reaction mixture to form and precipitate a salt of the 1,2,4,5-tetraminobenzene, wherein the acid is selected from the group consisting of HCl, acetic acid, $H_2SO_4$, and $H_3PO_4$;

(k) cooling, filtering, washing and dissolving the precipitated 1,2,4,5-tetraminobenzene salt to form an aqueous solution thereof;

(l) combining the filtered reaction mixture with
  (i) 0 to 5 equivalents of an acid selected from the group consisting of HCl, acetic acid, $H_2SO_4$ and $H_3PO_4$;
  (ii) 0 to 5 equivalents of an organic base or an inorganic base;
  (iii) optionally, a buffer solution; and
  (iv) an XYTA source selected from XYTA and $M_2$XYTA as represented by the structure of the following Formula (III):

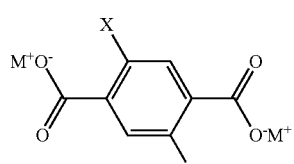

wherein M is K or Na, and wherein the molar ratio of XYTA to the 1,2,4,5-tetraminobenzene salt is from 1:1 to 1:1.1;

to adjust the pH of the mixture to between about 3 and about 10, and to produce and precipitate a Formula (I) complex; and (m) cooling, filtering and washing the precipitated complex.

The process hereof is designed in such a way that solids handling is avoided. Filtered materials are transferred, without prior drying, in the form of suspension slurries in the solvent that is used for the respective reaction step. This process design thereby avoids costly drying processes. It also avoids the handling of solid materials with possible skin sensitizing properties and toxicity, and eliminates human and environmental exposure to them.

In a further alternative embodiment of a process hereof, in the formation of a 1,2,4,5-tetraminobenzene.XYTA complex, either a feed of a 1,2,4,5-tetraminobenzene or a salt thereof, a feed of XYTA or $M_2$XYTA, or a feed of an acid or a base, or a reaction mixture in which a 1,2,4,5-tetraminobenzene.XYTA complex is formed, may contain a reducing agent. A reducing agent is useful to reduce oxidation byproducts at the pH of the mixture in which the 1,2,4,5-tetraminobenzene, or a salt thereof, or the complex thereof, is formed or contained.

If the pH of the mixture containing the 1,2,4,5-tetraminobenzene or complex is less than 7.0, the reducing agent is typically selected from one or more members of the group consisting of Cr(II), Mn(II), Fe(0). Fe(II), Co(0), Co(II), Ni(0), Ni(II), Sn(0), Sn(II), Cu(0), Cu(I), Zn(0), Mg(0); and/or, if the pH of the mixture is 7.0 or more, the reducing agent is typically selected from one or more members of the group consisting of $Na_2S_2O_4$, $Na_2SO_3$, hydroxylamine-O-sulfonic acid)/KOH, a hydrazine, a hydroxylamine or salts thereof, and aluminum. These reducing agents are typically used in an amount of at least about 0.5 wt % and less than about 10 wt %, preferably less than about 5 wt %, and, more preferably, less than about 3 wt % based on the weight of 1,2,4,5-tetraminobenzene or the complex.

A mixture containing a 1,2,4,5-tetraminobenzene, or a salt thereof, or complex thereof, may also contain a miscible co-solvent such as an alcohol. Suitable alcohols include methanol, ethanol and isopropanol and the like.

Any or all steps of any of the above processes may be run under the exclusion, or substantial exclusion, of oxygen, which may be accomplished, for example, by running under nitrogen. A substantial exclusion of oxygen exists when, in the formation of a 1,2,4,5-tetraminobenzene, or in the formation of succeeding materials into which the a 1,2,4,5-tetraminobenzene is converted, there has been the corresponding formation of less than 10,000, or less than 8,000, or less than 6,000, or less than 4,000, or less than 2,000, or less than 1,000, or less than 750, or less than 500, or less than 250 total ppm of all byproducts resulting from oxidataive degradation, including without limitation oxidation species such as 3,6-diiminocyclohexa-1,4-diene-1,4-diamine (Formula IV), and phenazine-2,3,7,8-tetraamine (Formula V):

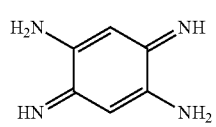

IV

-continued

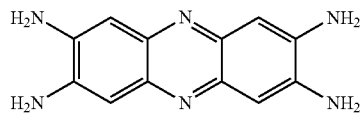

V

In any of the embodiments hereof, a solvent suitable for use includes an organic solvent inert to the reaction such as an aliphatic dihydric alcohol such as ethylene glycol ("glycol").

One particular embodiment of a process hereof is illustrated in FIG. 1 wherein the process starts with the nitration 1 of 1,3-dihalobenzene ["mDHB" (i.e. 1,3-dichlorobenzene or 1,3-dibromobenzene; 1,3-dichlorobenzene is preferred)] in a reaction mixture prepared by combining the 1,3-dihalobenzene 2; sulfuric acid; oleum 3 or $SO_3$ 5; and nitric acid 4. The concentration of nitric acid is about 2.0 to about 2.3 moles per mole of 1,3-dihalobenzene. Concentrated nitric acid (e.g. commonly used reagent grade, which is about 70% nitric acid in water) can be used, but fuming nitric acid is preferred. Fuming nitric acid is concentrated nitric acid containing dissolved nitrogen dioxide The concentration of $SO_3$ is about 1 to about 3 moles, preferably 1.5 to 2 moles, per mole of 1,3-dihalobenzene. If concentrated nitric acid is used, more $SO_3$ would be added than would ordinarily be needed for the nitration reaction to remove the water from the nitric acid (by reaction with it to form sulfuric acid). In a process hereof, it is desired to keep water at a level below one equivalent to get highly pure product. $SO_3$ may be added as $SO_3$, or in the form of oleum, which is fuming sulfuric acid, which is anhydrous and is formed by dissolving excess sulfur trioxide ($SO_3$) into sulfuric acid. The sulfuric acid is present in an amount such that the weight percent of mDHB in the reaction mixture (i.e. the weight of mDHB relative to the combined weight of mDHB plus all other components of the reaction mixture) is between 12 and 24 weight percent.

The nitration reaction is carried out at a temperature not to exceed about 120° C., typically in the range of about 5° C. to about 100° C., preferably in the range of about 5° C. to about 40° C., and more preferably in the range of about 5° C. to about 15° C. The 1,3-dihalo-4,6-dinitrobenzene thereby produced is separated directly by filtration 6 from the reaction mixture as a crude crystal cake without quench or recrystallization steps. The crude crystal cake is washed (9, 10) with water or with acid (e.g. concentrated or dilute sulfuric acid) then water; and is then washed with $NH_4OH$. Aqueous waste is discarded 8. The sulfuric acid mother liquor is recycled 7, 1 with a purge drawn to prevent excess sulfuric acid accumulation. The resulting wet cake of 1,3-dihalo-4,6-dinitrobenzene is then mixed with a solvent such as glycol 12 and introduced into the amination reactor 11 as a suspension.

The suspension is heated to a temperature in the range of about 100° C. to about 160° C., preferably about 140° C., to dissolve the 1,3-dihalo-4,6-dinitrobenzene in glycol or other solvent. The resulting solution is contacted at that temperature with gaseous $NH_3$ 13 for approximately four to eight hours close to ambient pressure; the $NH_3$ is fed as it is consumed. At reaction completion, the 1,3-diamino-4,6-dinitrobenzene thereby produced is filtered 14, typically at about 60° C., and washed with glycol or other solvent 15 and then water 16. The mother liquor (filtrate) containing glycol is collected 17a, and the glycol is distilled and recycled 17b, 15; purges are drawn to prevent accumulation. The wet cake of 1,3-diamino-4,6-dinitrobenzene is slurried with water 19 and transferred to the hydrogenation reactor 18 as a suspension.

The hydrogenation reactor also contains a hydrogenation catalyst 22. Suitable hydrogenation catalysts comprise metal and/or metal salt; examples include without limitation Pd/C and Pt/C and mixtures thereof, optionally containing other metals from Groups VIII through X such as Fe. The groups are as described in the Periodic Table in *Advanced Inorganic Chemistry* by Cotton and Wilkinson, Interscience New York, 2nd Ed. (1966). Of these, Pt/C is preferred. The catalyst is typically used in the amount of about 0.5 to about 5.0 wt % metal based on the weight of 1,3-diamino-4,6-dinitrobenzene.

The hydrogenation reactor is purged with nitrogen, and the aqueous suspension is contacted with hydrogen 21 in the presence of about 0 to about 1 mol equivalent of $NH_{3(g)}$ 20 to form a reaction mixture. The reaction is carried out at a temperature in the range of about to 20° C. to 100° C., preferably about 60° C. to about 85° C., and a hydrogen pressure of about 45 to about 500 psi (0.31 to 3.45 MPa) preferably about 300 psi (2.07 MPa). Reaction continues for a time sufficient to consume about 6 to 7 mol equivalents of hydrogen, thereby producing 1,2,4,5-tetraminobenzene ("TAB"). The time required depends on the details of the specific set up but is typically about 2 hours.

As shown in FIG. 1, about 1 to about 6 equivalents, preferably about 1 to about 3 equivalents, of an acid 23 are added to dissolve the TAB; as a result, a soluble acid salt of TAB is formed, herein referred to as "TAB salt." Any acid which allows for the dissolution of TAB in water and its subsequent re-precipitation is suitable, and the selection of the acid may be based on solubility data. Examples of suitable acids include without limitation HCl, acetic acid, $H_2SO_4$, and $H_3PO_4$. HCl is preferred, and the TAB salt generally prepared is TAB.4HCl. The solution may be heated to facilitate dissolution. Optionally, a co-solvent may be present. Examples of co-solvents include without limitation an alcohol such as methanol, ethanol, and isopropanol. Optionally, the solution may be filtered through an absorbent material capable of absorbing impurities. Examples of absorbent materials include without limitation active carbon, alumina and microporous styrene.

The resulting reaction mixture 24 is then filtered 25, typically at a temperature in the range of about 60° C. to about 80° C. to remove the spent hydrogenation catalyst 26, preferably by passing through a carbon filter bed. The spent catalyst can then be recycled.

Because the filtered reaction mixture may have picked up small amounts of oxygen, nitrogen 36 is typically blown through it 34 in a deoxygenation step. A small amount of tin 37 (e.g. about 0.5 wt % tin powder) may be added as well to reduce oxidized species and prevent additional oxidation. The temperature at this stage is typically about 35° C. to about 40° C.

The complex TAB.XYTA (Formula I) is produced by combining the filtered, deoxygenated reaction mixture with about 1 to about 5 equivalents of a source of the XYTA moiety 39 and adjusting the pH to precipitate the complex. This is done under a nitrogen atmosphere 43 to exclude oxygen. The XYTA source can be the diacid XYTA, the salt $M_2XYTA$ (M=K or Na), or a mixture of diacid XYTA and salt $M_2XYTA$. The pH is adjusted to between about 3 and about 10, preferably between about 5 and about 8, i.e. the pH range at which the complex is least soluble, to precipitate the desired 1:1 complex and maximize yield. The pH is adjusted to the desired value using 0 to 5 equivalents of an acid; 0 to 5 equivalents of a base such as an organic base or an inorganic base; and, optionally, a buffer solution. Water may be used as well.

Examples of suitable acids include without limitation HCl, acetic acid, $H_2SO_4$, and $H_3PO_4$. Examples of suitable organic bases include without limitation aliphatic amines (for example, triethylamine) and carboxylates like acetate (which may, if desired, be used in conjunction with a stronger base). Examples of suitable inorganic bases include without limitation KOH, NaOH, alkali carbonates, alkali bicarbonates, and ammonia. The acids and/or bases should not form undesirable products irreversibly when added to the reaction mixture. Also, any salt byproducts produced during complex formation should be readily removable (e.g. soluble in the reaction mixture or extractable with a solvent that does not dissolve the complex).

In the embodiment shown in FIG. 1, streams of water 40 and a basic solution 41 (for example, 2 equivalents NaOH) are added. The temperature of the mixture is initially about 40° C. to about 100° C., typically about 50° C. to about 60° C., and is gradually cooled to promote complete precipitation of the complex. The preferred precipitation temperature will depend on the product concentration and on the amount of impurities present, but is generally chosen between about 0° C. and about 40° C., preferably between about 0° C. and about 20° C.

Various designs are possible for combining the TAB salt solution with the XYTA source and whatever acid, base, and/or buffer solutions are used to adjust the pH. FIG. 1 shows one embodiment in which a stream of TAB salt in an acid solution 34, the XYTA source 39, water 40, and base 41 are fed concurrently or consecutively into a vessel 38 wherein complex formation and precipitation take place. The XYTA source 39, water 40, and base 41 are most conveniently added as a single solution. In other embodiments, TAB salt in an acid solution could be introduced into a vessel containing a basic XYTA source solution, or the XYTA source stream could be fed into the vessel containing the TAB salt in an acid solution. Alternatively, the XYTA source and TAB salt could be fed concurrently or consecutively into a buffer solution at the desired pH or into a basic solution to which an acid solution is subsequently added.

The TAB.XYTA complex is recovered from the reaction mixture by filtration at a temperature in the range of about 5° C. to about 50° C., preferably about 10° C. to about 15° C., and washed with water 45 and methanol 47, typically at a temperature in the range of about 15° C. to about 40° C. The methanol is recycled (47, 48) and a purge is drawn to prevent accumulation. Aqueous wastes are discarded. In the embodiment shown in FIG. 1, there are two purge streams for aqueous wastes (42, 46), one of which (42) contains most of the Sn used in the deoxygenation step. The washed and dried TAB.XYTA complex 50 is kept under nitrogen 49 to protect it from oxygen. It is of high enough quality and purity to produce polybenzimidazole polymer of high enough molecular weight to make high performance fibers.

Figure 2:
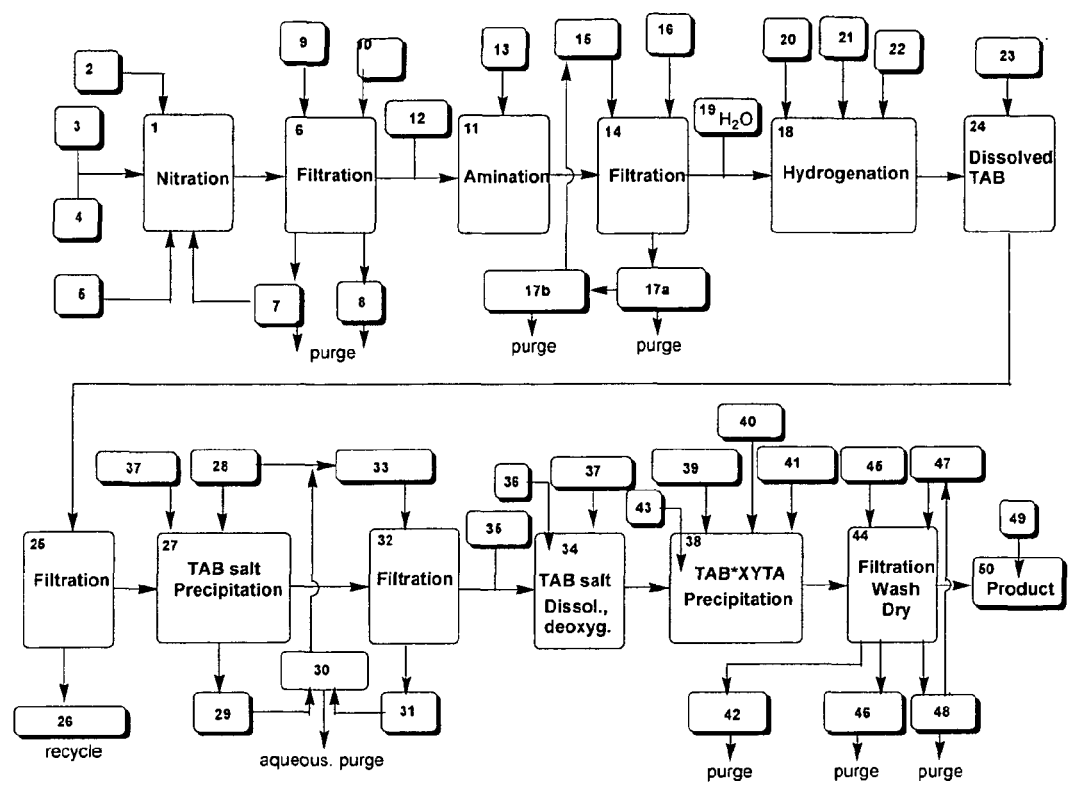
FIG. 2 is a schematic representation of another embodiment of the process described herein.

In another embodiment of the process described herein, illustrated in FIG. 2, acid is added 28 at a temperature in the range of about 10° C. to about 80° C. to form and precipitate the TAB salt 27, for example, TAB.4HCl. Examples of suitable acids include without limitation HCl, acetic acid, $H_2SO_4$, and $H_3PO_4$. HCl is preferred. The amount of acid needed for this step may be determined based on the concentration of TAB in the filtrate. Typically, about 6 to about 8 equivalents of acid (as for example, 38% $HCl_{aq}$) are needed in this step to precipitate the TAB salt (for example, as TAB.4HCl) in about 90% yield. The use of gaseous acid, such as gaseous HCl, may be desired to reduce the total volume of liquid needed since the additional introduction of water with aqueous acid in both addition steps increases the absolute solubility of the TAB salt in the filtered reaction mixture. The addition of equivalent amounts of acid in the gas phase instead of as an aqueous solution (for example, $HCl_{gas}$ instead of $HCl_{aq}$) may be preferred since the liquid volumes are thereby reduced, and crystallization yields are expected to be higher as a consequence. Aqueous acid (for example, 30-38 wt % HCl) may be used because it is easier to handle than the acid in the gas phase. Aqueous acid can be recovered 29, distilled 30, and recycled (30, 28) or used in the acid wash step of the process (30, 33, 44).

A small amount of tin (e.g., about 0.5% tin powder) is optionally added 37 to reduce impurities caused by oxidation and to prevent further impurity formation by that route.

The reaction mixture containing the precipitated TAB salt is then cooled to about 5° C. to about 15° C. and stirred, then filtered 32. The TAB salt is then washed with deaerated aqueous acid, such as concentrated HCl 33. The used aqueous acid can then be distilled and recycled (31, 30, 33). Water is added 35 to dissolve the washed TAB salt 34. Although filtration 32 and salt dissolution 34 are shown as occurring in separate vessels in the embodiment illustrated in FIG. 2, a single vessel could be used. After the TAB salt is dissolved 34, the TAB.XYTA formation and precipitation, filtration, washing, and drying are carried out as described above (36 through 50).

The embodiment illustrated in FIG. 2 can produce good purity TAB.XYTA complex without the need to use carbon bed filters and allows for more flexibility in terms of production (timing) and easier dosage. The embodiment illustrated in FIG. 1, on the other hand, reduces the amount of waste salt and also the amount of acid (e.g. HCl) and base (e.g. NaOH) needed, thus lessening raw material cost. Both embodiments produce polymer grade material suitable for the manufacture of high-performance fibers.

The process described herein is an efficient and effective way to produce high purity TAB.XYTA complexes, particularly the 1:1 complex of TAB and 2,5-dihydroxyterephthalic acid, which can be used to make polybenzimidazole polymer for high performance fibers. This process design eliminates costly intermediate drying and recrystallization steps. The recycling of spent catalyst and of sulfuric acid, glycol, and methanol streams contributes economical and environmental advantages. And, importantly, handling of solid materials with possible skin sensitizing properties and toxicity is avoided, thereby eliminating human and environmental exposure.

In yet another embodiment, a TAB.XYTA complex may be converted to a polymer such as a pyridobisimidazole-2,6-diyl (2,5-dihydroxy-p-phenylene) polymer by polymerization in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by polymerization at a temperature from about 50° C. to about 110° C., and then 145° C. to form an oligomer, and then reacting the oligomer at a temperature of about 160° C. to about 250° C. as disclosed in U.S. Patent Publication 2006/0287475 (which is by this reference incorporated in its entirety as a part hereof for all purposes). The pyridobisimidazole-2,6-diyl(2,5-dihydroxy-p-phenylene) polymer so produced may be, for example, a poly(1,4-(2,5-dihydroxy)phenylene-2,6-pyrido[2,3-d: 5,6-d']bisimidazole) polymer, or a poly[(1,4-dihydrodiimidazo[4,5-b:4',5'-e]pyridine-2,6-diyl) (2,5-dihydroxy-1,4-phenylene)] polymer. The pyridobisimidazole portion thereof may, however, be replaced by any or more of a benzobisimidazole, benzobisthiazole, benzobisoxazole, pyridobisthiazole and a pyridobisoxazole; and the 2,5-dihydroxy-p-phenylene portion thereof may be replace the derivative of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole.

EXAMPLES

The advantageous attributes and effects of the processes hereof may be seen in a series of examples as described below. The embodiments of these processes on which the examples are based are representative only, and the selection of those embodiments to illustrate the invention does not indicate that materials, reactants, conditions, steps, techniques, or protocols not described in these examples are not suitable for practicing these processes, or that subject matter not described in these examples is excluded from the scope of the appended claims and equivalents thereof.

In the examples, the meaning of certain abbreviations is as follows: "d" means density, "DADNB" means 1,3-diamino-4,6-dinitrobenzene, "DCDNB" means 1,3-dichloro-4,6-dinitrobenzene, "equiv" means equivalent(s), "g" means gram(s), "gal" means gallon, "GC" means gas chromatography, "$^1$H-NMR" means proton nuclear magnetic resonance spectroscopy, "h" means hour(s), "L" means liter(s), "mL" means milliliter(s), "min" means minutes, "mol" means mole(s), "MPa" means megapascals, "psi" means pounds per square inch, and "UV" means ultraviolet spectroscopy.

As used herein, the term "net yield" of product denotes the actual, in-hand yield, i.e., the theoretical maximum yield minus losses incurred in the course of activities such as isolating, handling, drying, and the like. As used herein, the term "purity" denotes what percentage of an in-hand, isolated sample is actually the specified substance.

Example 1

Preparation of Dcdnb Wet Cake

To a 1 L 3-neck round bottom flask equipped with external ice cooling, mechanical stirrer, addition funnel, $N_2$ inlet, and thermometer was added 126 g (2 mol) fuming nitric acid (d=1.54), followed by 208 g sulfuric acid and 508 g 30% oleum (2.2 molar equiv $SO_3$) maintaining a temperature between 10 and 40° C. Subsequently, 140 g (0.95 mol) 1,3-dichlorobenzene (Toray Ltd., Tokyo, Japan, >99% purity) were added over a time period of 90 min while maintaining a temperature of about 5° C. The ice bath was removed, and the reaction mixture was allowed to warm up to room temperature. It was then heated from room temperature to 100° C. over a time period of 45 min.

At that point, a small sample of crude product was taken from the reaction vessel and poured into ice water. The crude product was extracted with methylene chloride. Analysis by GC and $^1$H-NMR indicated a reaction selectivity to 1,3-dichloro-4,6-dinitrobenzene of 92%. After 15 min at 100° C., the reaction mixture was allowed to cool to room temperature over 2 h and then cooled to 5° C. over 30 min, after which it was filtered through a glass fritted funnel and washed with 300 mL water followed by 200 mL 10% aqueous $NH_3$ solution. Analysis indicated a net content of about 184 g of >98% pure product (~80% net yield), and the dry mass content of the wet cake was about 90%.

Example 2

Preparation of Dadnb Wet Cake

A three-necked 2 L flask was equipped with a thermocouple, magnetic stirrer and gas inlet tube and reflux condenser with gas outlet. The gas outlet was equipped with a three-way-splitter connecting the outlet to an oil bubbler and an $N_2$ line. The inlet tube was connected to an oil bubbler, a wash bottle and a three-way-splitter connected to $N_2$ and a $NH_3$ bottle. The wet DCDNB (184 g net product weight prepared as described in Example 1) was suspended in 1200 mL glycol (1% water). The water content of the mixture was about 1.5-2%. Nitrogen was purged through the inlet tube for 2 h under stirring before the mixture was heated to 140° C. The gas purge was switched to $NH_3$, and the flow rate was adjusted such that the amount released through the gas outlet was kept at minimum.

During the course of the reaction the product DADNB precipitated as a yellow-to-amber fine crystalline material. Conversion to product was controlled by GC analysis. After delivering about 6 equivalents of $NH_3$ the reaction solution showed less than 1% 1-amino-5-chloro-2,4-dinitrobenzene, the nitrogen purge at the gas outlet was turned up and the ammonia flow was turned off and the feed tube was removed. The reaction suspension was allowed to cool to 60° C. before it was filtered, and the yellow-to-bronze colored fine crystalline product was washed with two portions of about 50 mL of 60° C. ethylene glycol followed by 2×50 mL water. The net yield was about 95% and the purity was >99%. The dry mass content of the wet cake was about 88%.

Example 3

Preparation of TAB.2HCl

A 1 gal (3.79 L) stirred Hastelloy autoclave was charged with 547 g of DADNB wet cake (480 g DADNB, 67 g water) prepared as described in Examples 1 and 2, and 9.6 g of 5% Pt/C (dry basis, 50% water). The autoclave was purged 5 times with $N_2$ and 2 times with H, at 90 psi (0.62 MPa). Subsequently, 2200 mL of deaerated water (purged with $N_2$ overnight) were added and the mixture was pressurized at 81° C. to 300 psi (2.07 MPa). Hydrogenation was continued for a total time of about 3 h with an approximate uptake of 16 moles of $H_2$ (6.5 equiv). The excess hydrogen was released and the autoclave was cooled to 40° C. and purged twice with $N_2$, after which 489 g of deaerated $HCl_{aq}$ (36.3%, by titration) was added. The mixture was stirred and heated back up to 80° C., then passed through a carbon bed filter at about 65° C. to remove catalyst and a small amount of unconverted starting material. The TAB.2HCl solution was directly charged into a holdup vessel under $N_2$ containing 5 g of Sn powder.

Example 4

Preparation of TAB.DHTA 43.99 g of $K_2$DHTA (160.38 mmol) along with 3.849 g of sodium hydroxide (96.227 mmol) was added to a reaction vessel. This was followed by the addition of 480 mL of deaerated water and heating to 65° C. About 271 g aqueous TAB.2HCl salt solution made as described in Example 3 (equivalent to net 41 g of 1,3-diamino-4,6-dinitrobenzene) was combined with 60 g of deaerated water and 283 mg of tin powder (2.41 mmol) heated to 65° C. to affect complete dissolution. The TAB salt solution was subsequently pumped into the basic $K_2$DHTA solution over a period of 30 minutes, which resulted in precipitation of a pink solid. This mixture was then cooled to 15° C. with stirring for 1.5 hours. The mixture was subsequently filtered and washed with water (200 mL) and methanol (250 mL). The solid light pink product was allowed to dry for 30 hours under a stream of nitrogen at 40° C.

The net yield was 50.1 g (96%). $^1$H-NMR analysis indicated product purity >99% with a TAB:DHTA ratio of 1.00:1.00. The material was analyzed by UV for oxidative decomposition products such as 3,6-diiminocyclohexa-1,4-diene-1,4-diamine (Formula II) and phenazine-2,3,7,8-tetraamine (Formula V). No Formula V compound, and less than 100 ppm of Formula IV compound, was detected.

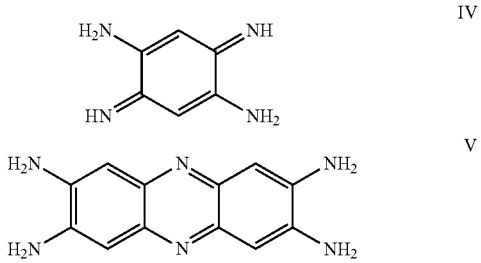

Examples 5-9

In Examples 5-9, the 1,2,4,5-tetraminobenzene.4HCl was made according to the following process:

Contacting 1,2,4,5-tetraminobenzene with an aqueous solution comprising 1 to 6 equivalents of acid per mol of 1,2,4,5-tetraminobenzene, optionally heating the solution, thereby dissolving the 1,2,4,5-tetraminobenzene; forming and precipitating the 1,2,4,5-tetraminobenzene salt by adding an acid to the dissolved 1,2,4,5-tetraminobenzene, and washing the 1,2,4,5-tetraminobenzene salt, wherein all steps are performed under oxygen exclusion.

The dipotassium salt of 2,5-dihydroxyterephthalic acid ("$K_2$DHTA") was made according to the method described in U.S. Pat. No. 6,040,478[(C3, L47-59), which is by this reference incorporated in its entirety herein for all purposes]. Its purity was between 98 and 99.8% with the major impurity potassium formate. The $K_2$DHTA was dried to constant weight at 70° C. under vacuum to remove water.

Sodium hydroxide ("NaOH") was of 99% purity. Tin powder (99% purity) and iron powder (99% purity) were obtained from Sigma-Aldrich (Milwaukee, Wis., USA). All water used was deaerated and de-ionized water. The processes were run under the exclusion of oxygen.

Example 5

This example demonstrates the preparation of a high-purity complex of 1,2,4,5-tetraminobenzene with 2,5-dihydroxyterephthalic acid dipotassium salt in the presence of Sn powder as a reducing agent. All operations were performed in a glovebox with oxygen excluded.

2,5-Dihydroxyterephthalic acid dipotassium salt ("$K_2$DHTA", 0.459 g, 1.00 equiv, 1.673 mmol) was weighed into a 20 mL vial. Sodium hydroxide (0.141 g, 2.1 equiv., 3.513 mmol) was weighed into a 1 dram (3.7 mL) vial. The sodium hydroxide was added to the $K_2$DHTA using deaerated and de-ionized water (7.5 g). The resulting mixture was added to a 40 mL scintillation vial and stirred. The $K_2$DHTA dissolved quickly in the presence of the sodium hydroxide. The resulting solution, Solution A, was yellow in color. Solution A was then heated at 50° C. with stirring for 15 minutes.

1,2,4,5-Tetraminobenzene.4HCl ("TAB.4HCl" 499 mg, 1.757 mmol, 1.025 equiv.) was dissolved in deaerated and de-ionized water (7.5 g) and warmed to 50° C. while stirring. To the TAB.4HCl was added Sn powder (0.005 g, 0.0418 mmol, 0.025 equiv). The solution was translucent with a yellow tinge. Solution B was slowly added over 10 minutes to Solution A. After addition, the Solution B vial was washed with another 0.5 mL of water at room temperature and transferred over and stirred at 1000 rpm for 1.5 hours at room temperature.

A white precipitate formed and was separated by vacuum filtration, then washed with water (5 mL) and methanol (5 mL) and dried under vacuum. NMR analysis showed the precipitate to be a 1.00:1.00 TAB.DHTA complex with no evidence of oxidation. Net yield was 433 mg, or 77%.

Example 6

This example demonstrates a larger-scale preparation of a high-purity complex of 1,2,4,5-tetraminobenzene with 2,5-dihydroxyterephthalic acid dipotassium salt in the presence of Sn powder as a reducing agent.

TAB.4HCl (450 g, 1.584 mol, 1.1 equiv) was added to a 3 L reactor along with tin powder (2.5 g, 0.0211 mol, 0.015 equiv) and purged with nitrogen to ensure an inert atmosphere. To this vessel was added deaerated water (2700 g). The solution was heated to 54° C. In a separate 6 L vessel, $K_2$DHTA (395.1 g, 1.44 mol, 1 equiv) and NaOH (138.28 g, 3.457 mol, 2.4 equiv) were combined, purged thoroughly with nitrogen, dissolved in water (3500 g) and heated to 65° C. The TAB.4HCl solution was added to the $K_2$DHTA/NaOH solution over 35 minutes which resulted in the formation of a flocculant light yellow precipitate. This mixture was then cooled to 15° C. over 90 minutes while stirred. The light yellow solid was recovered by filtration, washed with water (500 mL) and methanol (700 mL), and was dried overnight at 30° C. This provided 463 g (96% net yield) of a light yellow solid. NMR analysis indicated a 1.00:1.00 ratio of TAB to DHTA.

Example 7

This example demonstrates the preparation of a high-purity complex of 1,2,4,5-tetraminobenzene with 2,5-dihydroxyterephthalic acid dipotassium salt in the presence of Fe powder as a reducing agent. All operations were performed in a glovebox with oxygen excluded.

2,5-Dihydroxyterephthalic acid dipotassium salt ("$K_2$DHTA," 0.459 g, 1.00 equiv, 1.673 mmol) was weighed into a 20 mL vial. Sodium hydroxide (0.141 g, 2.1 equiv, 3.513 mmol) was weighed into a 1 dram (3.7 mL) vial. The sodium hydroxide was added to the $K_2$DHTA using deaerated and de-ionized water (7.5 g). The resulting mixture was added to a 40 mL scintillation vial and stirred. The $K_2$DHTA dissolved quickly in the presence of the sodium hydroxide. The resulting solution, Solution A, was yellow in color. Solution A was then heated at 50° C. with stirring for 15 minutes.

1,2,4,5-Tetraminobenzene.4HCl ("TAB.4HCl" 499 mg, 1.757 mmol, 1.025 equiv.) was dissolved in deaerated and de-ionized water (7.5 g) and warmed to 50° C. while stirring. To the TAB.4HCl was added Fe powder (0.00234 g, 0.418 mmol, 0.025 equiv.). This solution, Solution B, was dark blue in color before the Fe powder was added and became almost light green after the addition of the Fe powder. Solution B was slowly added over 10 minutes to Solution A. After addition, the Solution B vial was washed with another 0.5 mL of water at room temperature and transferred over and stirred at 1000 rpm for 1.5 hours at room temperature.

A white precipitate formed and was separated by vacuum filtration, then washed with water (5 mL) and methanol (5 mL) and dried overnight under vacuum. The dried precipitate was ground up and dried again under vacuum. The material was white. NMR analysis of the white material showed it to be a 1.00:1.00 TAB.DHTA complex with no evidence of oxidation byproducts. Net yield was 484 mg, or 86%.

Example 8

This example demonstrates a larger-scale preparation of a high-purity complex of 1,2,4,5-tetraminobenzene with 2,5-dihydroxyterephthalic acid dipotassium salt in the presence of Sn powder and sodium hydrosulfite as reducing agents.

TAB.4HCl (45.12 g, 0.159 mol, 1.1 equiv) was added to a 500 mL reactor along with tin powder (0.257 g, 0.00217 mol, 0.015 equiv) and purged with nitrogen to ensure an inert atmosphere. To this vessel was added deaerated water (300 g). The solution was heated to 55° C. In a separate 1 L vessel, $K_2$DHTA (39.62 g, 0.144 mol, 1 equiv), sodium hydrosulfite (0.629 g, 0.0036 mol, 0.025 eq) and NaOH (13.866 g, 0.347 mol, 2.4 equiv) were combined, purged thoroughly with nitrogen, dissolved in water (430 g) and heated to 55° C. The TAB.4HCl solution was added to the $K_2$DHTA/NaOH solution over 45 minutes which resulted in the formation of a flocculant light yellow precipitate. This mixture was then cooled to 15° C. over 90 minutes while being stirred. The light yellow solid was recovered by filtration, washed with water (200 mL) and methanol (250 mL), and was dried overnight at 40° C. This provided 48.4 g (100%) of a beige solid. NMR analysis indicated a 1.00:1.00 ratio of TAB to DHTA.

Example 9 and Comparative Example A

Example 9 and Comparative Example A demonstrate how polymer properties are affected by when a reducing agent (here, Sn) is added in the production process.

In Comparative Example A, the complex was prepared without tin. TAB.4HCl (45.1 g, 0.159 mol, 1.1 equiv) was added to a 500 mL reactor and purged with nitrogen to ensure an inert atmosphere. To this vessel was added deaerated water (300 g). The solution was heated to 56° C. In a separate 1 L vessel, $K_2$DHTA (39.6 g, 0.144 mol, 1 equiv) and NaOH (13.9 g, 0.347 mol, 2.4 equiv) were combined, purged thoroughly with nitrogen, dissolved in water (430 g) and heated to 65° C. The TAB.4HCl solution was added to the $K_2$DHTA/ NaOH solution over 35 minutes which resulted in the formation of a flocculant light pink precipitate. This mixture was then cooled to 15° C. over 90 minutes while being stirred. The light pink solid was recovered by filtration, washed with water (200 mL) and methanol (250 mL), and was dried overnight at 40° C. This provided 37.7 g (79% net yield) of a pink solid. NMR analysis indicated a 1.00:1.00 ratio of TAB to DHTA. The material was analyzed by UV for oxidative decomposition products such as 3,6-diiminocyclohexa-1,4-diene-1,4-diamine (Formula IV) and phenazine-2,3,7,8-tetraamine (Formula V). 3700 ppm of II and 5000 ppm of III were detected.

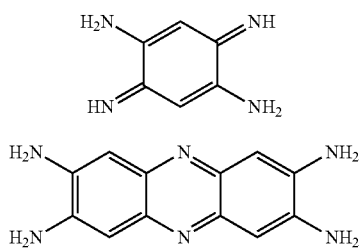

Samples of this TAB.DHTA complex and of the TAB.DHTA complex prepared in Example 2 were polymerized according to the protocol below.

Polymerization Protocol

Comparative Example A

Tin powder (12 mg) was weighed into a 20 mL vial and TAB.DHTA complex (2.54 g) subsequently added and mixed thoroughly. Phosphorus pentoxide (1.20 g) was added to a 40 mL vial along with 1 g of an o-phenylenediamine/polyphosphoric acid solution (5 mg/mL). This was followed by the addition of the tin/complex mixture and 15.2 g polyphosphoric acid (85%). The vials were placed on a reactor block equipped with an overhead mixer. The vials were then warmed to 50° C. and mixing started. The temperature was raised to 100° C. for 1 hour, 120° C. for 20 hours and then 180° C. for 2 hours. The mixing was then stopped and the polymer removed from the vial while still hot.

Example 5

The polymerization was carried out as described above, but without adding tin.

The inherent viscosity of each polymer was subsequently determined in methanesulfonic acid using a Canon-Fiske viscometer and reported as an average of three runs. Results are summarized in Table 1. Polymer made from TAB.DHTA complex that had been prepared without tin, but with tin (6000 ppm) added at the beginning of the polymerization, had an inherent viscosity of 21.2. Polymer made from TAB.DHTA complex that had been prepared with tin but with no tin added at any stage of the polymerization, had an inherent viscosity of 25, i.e. higher molecular weight. This demonstrates that adding a reducing agent (here, tin) at the complex formation stage instead of at the start of polymerization results in a higher molecular weight product.

TABLE 1

| TAB•DHTA Complex Prep. Method | TAB:DHTA Ratio | Yield (%) | Phenazine* (ppm) | Bis-imine** (ppm) | Tin added to polymerization (ppm) | IV |
|---|---|---|---|---|---|---|
| no tin | 1.00:1.00 | 79 | 5000 | 3700 | 6000 | 21.2 |
| with tin | 1.00:1.00 | 96 | <100 | 0 | 0 | 25 |

*phenazine-2,3,7,8-tetraamine
**3,6-diiminocyclohexa-1,4-diene-1,4-diamine

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

What is claimed is:

1. A process for preparing a complex that comprises 1,2,4,5-tetraminobenzene and the aromatic diacid XYTA [which is represented by the structure of the following Formula (I)]:

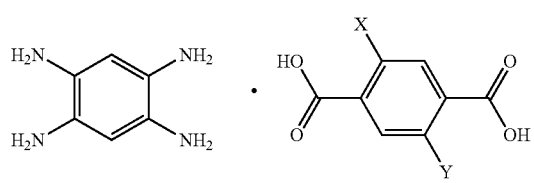

wherein X and Y are each independently selected from the group consisting of H, OH, SH, methyl, ethyl, F, Cl and Br; comprising (a) nitrating 1,3-dihalobenzene, which is represented by the structure of the following Formula (II):

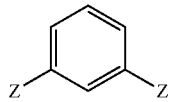

II wherein each Z is independently Cl or Br, to produce 1,3-dihalo-4,6-dinitrobenzene;
(b) heating a suspension of the 1,3-dihalo-4,6-dinitrobenzene, and contacting it with $NH_3$ to aminate the 1,3-dihalo-4,6-dinitrobenzene and convert it to 1,3-diamino-4,6-dinitrobenzene;
(c) forming a slurry of the 1,3-diamino-4,6-dinitrobenzene with water, and contacting the slurry with hydrogen and a hydrogenation catalyst to hydrogenate the 1,3-diamino-4,6-dinitrobenzene and produce 1,2,4,5-tetraminobenzene;
(d) contacting the 1,2,4,5-tetraminobenzene produced in (c) with an aqueous solution comprising 1 to 6 equivalents of acid per mol of 1,2,4,5-tetraminobenzene, and, optionally, heating the solution to dissolve the 1,2,4,5-tetraminobenzene; and
(e) combining the dissolved 1,2,4,5-tetraminobenzene with
(i) 0 to 5 equivalents of an acid;
(ii) 0 to 5 equivalents of a base;
(iii) optionally, a buffer solution; and
(iv) an XYTA source selected from XYTA and $M_2$XYTA as represented by the structure of the following Formula (III):

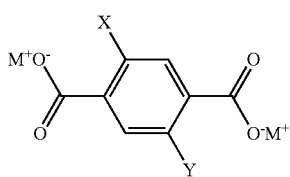

III wherein M is K or Na, and wherein the molar ratio of XYTA to the 1,2,4,5-tetraminobenzene salt is from 1:1 to 1:1.1; to adjust the pH of the mixture to between about 3 and about 10, and to produce and precipitate a Formula (I) complex.

2. A process according to claim 1 wherein the mixture containing the Formula (I) complex further comprises a reducing agent.

3. A process for preparing a complex that comprises 1,2,4,5-tetraminobenzene and the aromatic diacid XYTA [which is represented by the structure of the following Formula (I)]:

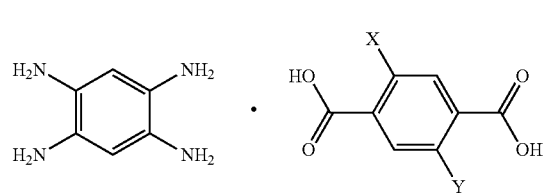

(I)

wherein X and Y are each independently selected from the group consisting of H, OH, SH, methyl, ethyl, F, Cl and Br; comprising
(a) nitrating 1,3-dihalobenzene, which is represented by the structure of the following Formula (II):

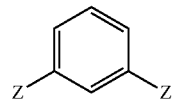

II wherein each Z is independently Cl or Br, in a reaction mixture comprising nitric acid, oleum or $SO_3$, and $H_2SO_4$, wherein
(i) the concentration of nitric acid is about 2.0 to about 2.3 moles per mole of 1,3-dihalobenzene;
(ii) the concentration of $SO_3$ is about 1 to about 3 moles per mole of 1,3-dihalobenzene; and
(iii) the concentration of 1,3-dihalobenzene in the reaction mixture is between about 12 and about 24 weight percent; and
(iv) the temperature of the reaction mixture does not exceed 120° C.;
to produce 1,3-dihalo-4,6-dinitrobenzene;
(b) filtering the reaction mixture to separate the 1,3-dihalo-4,6-dinitrobenzene therefrom, while recycling the sulfuric acid mother liquor;
(c) washing the 1,3-dihalo-4,6-dinitrobenzene with water, or acid then water, then with $NH_4OH$, and then mixing it with a solvent as a suspension;
(d) heating the suspension formed in step (c) to a temperature in the range of about 100° C. to about 160° C. and contacting it with $NH_3(g)$ to aminate the 1,3-dihalo-4,6-dinitrobenzene and convert it to 1,3-diamino-4,6-dinitrobenzene;
(e) filtering the reaction mixture to separate the 1,3-diamino-4,6-dinitrobenzene therefrom; and washing the 1,3-diamino-4,6-dinitrobenzene with a solvent and then water,
(f) forming a slurry of the 1,3-diamino-4,6-dinitrobenzene with water, and transferring the slurry to a hydrogenation reactor containing a hydrogenation catalyst to form a reaction mixture;
(g) contacting the reaction mixture formed in step (f) with hydrogen at a pressure in the range of about 0.31 to about 3.45 MPa and a temperature in the range of about 20° C. to about 100° C. to hydrogenate the 1,3-diamino-4,6-dinitrobenzene and produce 1,2,4,5-tetraminobenzene;
(h) contacting the 1,2,4,5-tetraminobenzene produced in (g) with an aqueous solution comprising 1 to 6 equivalents of acid per mol of 1,2,4,5-tetraminobenzene, and, optionally, heating the solution to dissolve the 1,2,4,5-tetraminobenzene;
(i) filtering the reaction mixture to remove the spent hydrogenation catalyst;
(j) combining the filtered reaction mixture with
(i) 0 to 5 equivalents of an acid selected from the group consisting of HCl, acetic acid, $H_2SO_4$ and $H_3PO_4$;
(ii) 0 to 5 equivalents of an organic base or an inorganic base;
(iii) optionally, a buffer solution; and
(iv) an XYTA source selected from XYTA and $M_2$XYTA as represented by the structure of the following Formula (III):

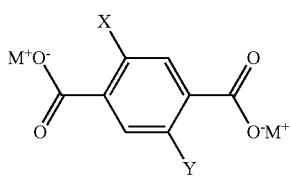

III wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex; and
(k) cooling, filtering and washing the precipitated complex.

4. A process according to claim 3 wherein X=Y=OH, M=K, Z=Cl, the acid in steps (h) and (j) is HCl, and the pH is adjusted to about 5 to about 8 in step (j).

5. A process according to claim 3 wherein the solvent used in step (e) is distilled and recycled.

6. A process according to claim 3 wherein the spent hydrogenation catalyst removed in step (i) is recovered and recycled.

7. A process according to claim 3 wherein, in step (k), the precipitated complex is washed with water and methanol, and the methanol is recycled.

8. A process according to claim 3 wherein the mixture containing the Formula (I) complex further comprises a reducing agent.

9. A process for preparing a complex that comprises 1,2,4,5-tetraminobenzene and the aromatic diacid XYTA [which is represented by the structure of the following Formula (I)]:

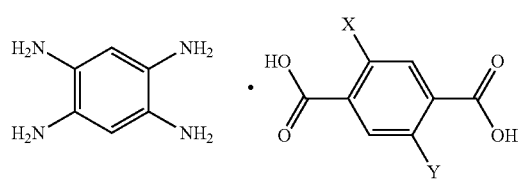

(I)

wherein X and Y are each independently selected from the group consisting of H, OH, SH, methyl, ethyl, F, Cl and Br; comprising
(a) nitrating 1,3-dihalobenzene, which is represented by the structure of the following Formula (II):

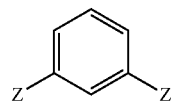

II wherein each Z is independently Cl or Br, to produce 1,3-dihalo-4,6-dinitrobenzene;
(b) heating a suspension of the 1,3-dihalo-4,6-dinitrobenzene, and contacting it with NH₃ to aminate the 1,3-dihalo-4,6-dinitrobenzene and convert it to 1,3-diamino-4,6-dinitrobenzene;
(c) forming a slurry of the 1,3-diamino-4,6-dinitrobenzene with water, and contacting the slurry with hydrogen and a hydrogenation catalyst to hydrogenate the 1,3-diamino-4,6-dinitrobenzene and produce 1,2,4,5-tetraminobenzene;

(d) contacting the 1,2,4,5-tetraminobenzene produced in (c) with an aqueous solution comprising 1 to 6 equivalents of acid per mol of 1,2,4,5-tetraminobenzene, and, optionally, heating the solution to dissolve the 1,2,4,5-tetraminobenzene;
(e) adding an acid to the dissolved 1,2,4,5-tetraminobenzene to form and precipitate a salt of the 1,2,4,5-tetraminobenzene;
(f) combining the precipitated salt of the 1,2,4,5-tetraminobenzene with
(i) 0 to 5 equivalents of an acid;
(ii) 0 to 5 equivalents of a base;
(iii) optionally, a buffer solution; and
(iv) an XYTA source selected from XYTA and M₂XYTA as represented by the structure of the following Formula (III):

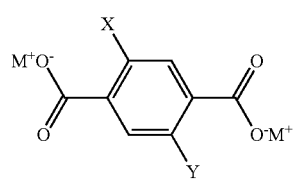

III wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex.

10. A process according to claim 9 wherein the mixture containing the Formula (I) complex further comprises a reducing agent.

11. A process for preparing a complex that comprises 1,2,4,5-tetraminobenzene and the aromatic diacid XYTA [which is represented by the structure of the following Formula (I)]:

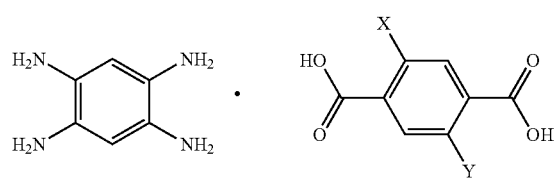

(I)

wherein X and Y are each independently selected from the group consisting of H, OH, SH, methyl, ethyl, F, Cl and Br; comprising
(a) nitrating 1,3-dihalobenzene, which is represented by the structure of the following Formula (II):

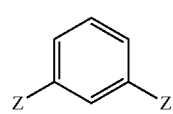

II wherein each Z is independently Cl or Br, in a reaction mixture comprising nitric acid, oleum or SO₃, and H₂SO₄, wherein (i) the concentration of nitric acid is about 2.0 to about 2.3 moles per mole of 1,3-dihalobenzene;
(ii) the concentration of $SO_3$ is about 1 to about 3 moles per mole of 1,3-dihalobenzene; and
(iii) the concentration of 1,3-dihalobenzene in the reaction mixture is between about 12 and about 24 weight percent; and
(iv) the temperature of the reaction mixture does not exceed 120° C.; to produce 1,3-dihalo-4,6-dinitrobenzene;
(b) filtering the reaction mixture to separate the 1,3-dihalo-4,6-dinitrobenzene therefrom, while recycling the sulfuric acid mother liquor;
(c) washing the 1,3-dihalo-4,6-dinitrobenzene with water, or acid then water, then with $NH_4OH$, and then mixing it with a solvent as a suspension;
(d) heating the suspension formed in step (c) to a temperature in the range of about 100° C. to about 160° C. and contacting it with $NH_3(g)$ to aminate the 1,3-dihalo-4,6-dinitrobenzene and convert it to 1,3-diamino-4,6-dinitrobenzene;
(e) filtering the reaction mixture to separate the 1,3-diamino-4,6-dinitrobenzene therefrom; and washing the 1,3-diamino-4,6-dinitrobenzene with a solvent and then water,
(f) forming a slurry of the 1,3-diamino-4,6-dinitrobenzene with water, and transferring the slurry to a hydrogenation reactor containing a hydrogenation catalyst to form a reaction mixture;
(g) contacting the reaction mixture formed in step (f) with hydrogen at a pressure in the range of about 0.31 to about 3.45 MPa and a temperature in the range of about 20° C. to about 100° C. to hydrogenate the 1,3-diamino-4,6-dinitrobenzene and produce 1,2,4,5-tetraminobenzene;
(h) contacting the 1,2,4,5-tetraminobenzene produced in (g) with an aqueous solution comprising 1 to 6 equivalents of acid per mol of 1,2,4,5-tetraminobenzene, and, optionally, heating the solution to dissolve the 1,2,4,5-tetraminobenzene;
(i) filtering the reaction mixture to remove the spent hydrogenation catalyst;
(j) adding an acid to the filtered reaction mixture to form and precipitate a salt of the 1,2,4,5-tetraminobenzene, wherein the acid is selected from the group consisting of HCl, acetic acid, $H_2SO_4$, and $H_3PO_4$;
(k) cooling, filtering, washing and dissolving the precipitated 1,2,4,5-tetraminobenzene salt to form an aqueous solution thereof;
(l) combining the filtered reaction mixture with
(i) 0 to 5 equivalents of an acid selected from the group consisting of HCl, acetic acid, $H_2SO_4$ and $H_3PO_4$;
(ii) 0 to 5 equivalents of an organic base or an inorganic base;
(iii) optionally, a buffer solution; and
(iv) an XYTA source selected from XYTA and $M_2$XYTA as represented by the structure of the following Formula (III):

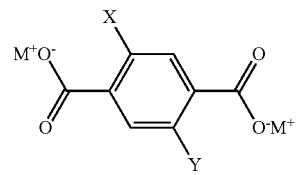

wherein M is K or Na, and wherein the molar ratio of XYTA to the 1,2,4,5-tetraminobenzene salt is from 1:1 to 1:1.1;
to adjust the pH of the mixture to between about 3 and about 10, and to produce and precipitate a Formula (I) complex; and
(m) cooling, filtering and washing the precipitated complex.

12. A process according to claim 11 wherein the acid in step (h) and/or (j) is HCl.

13. A process according to claim 11 wherein the acid in step (h) and/or (j) is added in the gaseous state.

14. A process according to claim 11 wherein the acid is added in step (j) an amount of about 6 to about 8 equivalents.

15. A process according to claim 11 wherein X=Y=OH, M=K, Z=Cl, the acid in step (h) and/or (j) is HCl, and the pH is adjusted to about 5 to about 8 in step (I).

16. A process according to claim 11 wherein the solvent used in step (e) is distilled and recycled.

17. A process according to claim 11 wherein the spent hydrogenation catalyst removed in step (i) is recovered and recycled.

18. A process according to claim 11 wherein, in step (m), the precipitated complex is washed with water and methanol, and the methanol is recycled.

19. A process according to claim 11 wherein the mixture containing the Formula (I) complex further comprises a reducing agent.

* * * * *